(12) United States Patent
Weber

(10) Patent No.: US 7,838,806 B2
(45) Date of Patent: Nov. 23, 2010

(54) RESONATOR WITH ADJUSTABLE CAPACITOR FOR MEDICAL DEVICE

(75) Inventor: Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 371 days.

(21) Appl. No.: 11/982,548

(22) Filed: Nov. 2, 2007

(65) Prior Publication Data

US 2008/0061788 A1 Mar. 13, 2008

Related U.S. Application Data

(63) Continuation of application No. 11/209,219, filed on Aug. 23, 2005.

(51) Int. Cl.
*H05B 6/36* (2006.01)

(52) U.S. Cl. .................. 219/674; 600/423; 324/322

(58) Field of Classification Search ............. 219/674, 219/660–666, 778–780; 600/410, 411, 413, 600/421–424, 428; 324/322, 307, 309, 318; 607/2, 4, 9, 57, 115, 116, 122
See application file for complete search history.

(56) References Cited

U.S. PATENT DOCUMENTS

| | | | |
|---|---|---|---|
| 4,685,462 A | 8/1987 | Olsen | |
| 5,049,821 A | 9/1991 | Duensing et al. | |
| 5,266,764 A * | 11/1993 | Fox et al. | 219/672 |
| 5,409,460 A | 4/1995 | Krumme | |
| 5,824,045 A | 10/1998 | Alt | |
| 5,843,117 A | 12/1998 | Alt et al. | |
| 5,855,600 A | 1/1999 | Alt | |
| 5,871,437 A | 2/1999 | Alt | |
| 6,027,510 A | 2/2000 | Alt | |
| 6,053,873 A | 4/2000 | Govari et al. | |
| 6,054,858 A | 4/2000 | Dumoulin et al. | |
| 6,099,561 A | 8/2000 | Alt | |
| 6,106,473 A | 8/2000 | Violante et al. | |
| 6,159,142 A | 12/2000 | Alt | |
| 6,159,237 A | 12/2000 | Alt et al. | |
| 6,231,516 B1 | 5/2001 | Keilman et al. | |

(Continued)

FOREIGN PATENT DOCUMENTS

WO WO 99/42039 8/1999

(Continued)

*Primary Examiner*—Quang T Van
(74) *Attorney, Agent, or Firm*—Brooks, Cameron & Huebsch, PLLC

(57) ABSTRACT

An apparatus, system and method of a resonator device with an adjustable capacitor for allowing the resonance frequency (F) of the resonator device to continue to be matched to the Larmor frequency of the MRI system. The resonator device includes an inductor coil, a conductive member, a sleeve having first and second sockets that receive at least portions of the inductor coil and the conductive member as electrodes to provide a capacitor structure. Dielectric material can be positioned between at least the first and second sockets, where changes in the cross sectional area defined by the induction coil cause changes in the capacitance value (C) as one or more of the electrodes move within the socket. Changes in the inductance and the capacitance values allow for the resonance frequency (F) of the resonator device to continue to be matched to the Larmor frequency of the MRI system.

7 Claims, 7 Drawing Sheets

U.S. PATENT DOCUMENTS

| | | |
|---|---|---|
| 6,245,104 B1 | 6/2001 | Alt |
| 6,251,134 B1 | 6/2001 | Alt et al. |
| 6,280,385 B1 | 8/2001 | Melzer et al. |
| 6,304,769 B1 | 10/2001 | Arenson et al. |
| 6,387,121 B1 | 5/2002 | Alt |
| 6,398,805 B1 | 6/2002 | Alt |
| 6,416,540 B1 | 7/2002 | Mathur |
| 6,463,317 B1 | 10/2002 | Kucharczyk et al. |
| 6,478,815 B1 | 11/2002 | Alt |
| 6,511,325 B1 | 1/2003 | Lalka et al. |
| 6,516,213 B1 | 2/2003 | Nevo |
| 6,574,497 B1 | 6/2003 | Pacetti |
| 6,585,660 B2 | 7/2003 | Dorando et al. |
| 6,585,755 B2 | 7/2003 | Jackson et al. |
| 6,585,763 B1 | 7/2003 | Keilman et al. |
| 6,628,980 B2 | 9/2003 | Atalar et al. |
| 6,652,540 B1 | 11/2003 | Cole et al. |
| 6,663,570 B2 | 12/2003 | Mott et al. |
| 6,668,197 B1 | 12/2003 | Habib et al. |
| 6,673,104 B2 | 1/2004 | Barry |
| 6,676,694 B1 | 1/2004 | Weiss |
| 6,702,847 B2 | 3/2004 | DiCarlo |
| 6,711,429 B1 | 3/2004 | Gilboa et al. |
| 6,711,440 B2 | 3/2004 | Deal et al. |
| 6,712,844 B2 | 3/2004 | Pacetti |
| 6,716,237 B1 | 4/2004 | Alt |
| 6,718,203 B2 | 4/2004 | Weiner et al. |
| 6,718,207 B2 | 4/2004 | Connelly |
| 6,725,092 B2 | 4/2004 | MacDonald et al. |
| 6,731,979 B2 | 5/2004 | MacDonald |
| 6,757,566 B2 | 6/2004 | Weiner et al. |
| 6,760,628 B2 | 7/2004 | Weiner et al. |
| 6,763,268 B2 | 7/2004 | MacDonald et al. |
| 6,765,144 B1 | 7/2004 | Wang et al. |
| 6,767,360 B1 | 7/2004 | Alt et al. |
| 6,778,856 B2 | 8/2004 | Connelly et al. |
| 6,782,284 B1 | 8/2004 | Subramanyan et al. |
| 6,786,904 B2 | 9/2004 | Doscher et al. |
| 6,795,730 B2 | 9/2004 | Connelly et al. |
| 6,795,736 B2 | 9/2004 | Connelly et al. |
| 6,799,069 B2 | 9/2004 | Weiner et al. |
| 6,802,811 B1 | 10/2004 | Slepian |
| 6,802,857 B1 | 10/2004 | Walsh et al. |
| 6,808,535 B1 | 10/2004 | Jordan |
| 6,819,954 B2 | 11/2004 | Connelly |
| 6,819,958 B2 | 11/2004 | Weiner et al. |
| 6,829,509 B1 | 12/2004 | MacDonald et al. |
| 6,844,492 B1 | 1/2005 | Wang et al. |
| 6,845,266 B2 | 1/2005 | Weiner et al. |
| 6,847,837 B1 | 1/2005 | Melzer et al. |
| 6,850,804 B2 | 2/2005 | Eggers et al. |
| 6,850,805 B2 | 2/2005 | Connelly et al. |
| 6,875,180 B2 | 4/2005 | Weiner et al. |
| 6,884,234 B2 | 4/2005 | Aita et al. |
| 6,892,090 B2 | 5/2005 | Verard et al. |
| 6,898,454 B2 | 5/2005 | Atalar et al. |
| 6,901,290 B2 | 5/2005 | Foster et al. |
| 6,908,468 B2 | 6/2005 | Daum |
| 6,925,322 B2 | 8/2005 | Helfer et al. |
| 6,925,328 B2 | 8/2005 | Foster et al. |
| 6,954,674 B2 | 10/2005 | Connelly |
| 6,957,098 B1 * | 10/2005 | Hyde et al. ................ 600/424 |
| 2001/0031919 A1 | 10/2001 | Strommer et al. |
| 2001/0031920 A1 | 10/2001 | Kaufman et al. |
| 2002/0019660 A1 | 2/2002 | Gianotti et al. |
| 2002/0026230 A1 | 2/2002 | Moll et al. |
| 2002/0045815 A1 | 4/2002 | Van Vaals |
| 2002/0045816 A1 | 4/2002 | Atalar et al. |
| 2002/0049375 A1 | 4/2002 | Strommer et al. |
| 2002/0082679 A1 | 6/2002 | Sirhan et al. |
| 2002/0082685 A1 | 6/2002 | Sirhan et al. |
| 2002/0137014 A1 | 9/2002 | Anderson et al. |
| 2002/0173724 A1 | 11/2002 | Dorando et al. |
| 2002/0188345 A1 | 12/2002 | Pacetti |
| 2003/0004562 A1 | 1/2003 | DiCarlo |
| 2003/0004563 A1 | 1/2003 | Jackson et al. |
| 2003/0074049 A1 | 4/2003 | Hoganson et al. |
| 2003/0083579 A1 | 5/2003 | Aita et al. |
| 2003/0087244 A1 | 5/2003 | McCarthy |
| 2003/0088178 A1 | 5/2003 | Owens et al. |
| 2003/0088308 A1 | 5/2003 | Scheurmann et al. |
| 2003/0092013 A1 | 5/2003 | McCarthy et al. |
| 2003/0096248 A1 | 5/2003 | McCarthy et al. |
| 2003/0099957 A1 | 5/2003 | McCarthy |
| 2003/0100830 A1 | 5/2003 | Zhong et al. |
| 2003/0105069 A1 | 6/2003 | Robinson et al. |
| 2003/0139739 A1 | 7/2003 | Doscher et al. |
| 2003/0143544 A1 | 7/2003 | McCarthy |
| 2003/0144728 A1 | 7/2003 | Scheuermann et al. |
| 2003/0163052 A1 | 8/2003 | Mott et al. |
| 2003/0187335 A1 | 10/2003 | McCarthy |
| 2003/0199747 A1 | 10/2003 | Michlitsch et al. |
| 2003/0212448 A1 | 11/2003 | Smith |
| 2004/0010304 A1 | 1/2004 | Weber et al. |
| 2004/0019376 A1 | 1/2004 | Alt |
| 2004/0030379 A1 | 2/2004 | Hamm et al. |
| 2004/0034300 A1 | 2/2004 | Verard et al. |
| 2004/0038406 A1 | 2/2004 | Unger et al. |
| 2004/0039438 A1 | 2/2004 | Alt |
| 2004/0044397 A1 | 3/2004 | Stinson |
| 2004/0059280 A1 | 3/2004 | Makower et al. |
| 2004/0082866 A1 | 4/2004 | Mott et al. |
| 2004/0091603 A1 | 5/2004 | Priewe |
| 2004/0093075 A1 | 5/2004 | Kuehne |
| 2004/0097804 A1 | 5/2004 | Sobe |
| 2004/0097805 A1 | 5/2004 | Verard et al. |
| 2004/0098093 A1 | 5/2004 | DiCarlo |
| 2004/0111016 A1 | 6/2004 | Casscells, III et al. |
| 2004/0116997 A1 | 6/2004 | Taylor et al. |
| 2004/0117007 A1 | 6/2004 | Whitbourne et al. |
| 2004/0122494 A1 | 6/2004 | Eggers et al. |
| 2004/0143180 A1 | 7/2004 | Zhong et al. |
| 2004/0158310 A1 | 8/2004 | Weber et al. |
| 2004/0186377 A1 | 9/2004 | Zhong et al. |
| 2004/0210289 A1 | 10/2004 | Wang et al. |
| 2004/0230271 A1 | 11/2004 | Wang et al. |
| 2004/0243220 A1 | 12/2004 | Gianotti et al. |
| 2004/0249428 A1 | 12/2004 | Wang et al. |
| 2004/0254419 A1 | 12/2004 | Wang et al. |
| 2004/0254632 A1 | 12/2004 | Alt et al. |
| 2005/0004653 A1 | 1/2005 | Gerberding et al. |
| 2005/0025797 A1 | 2/2005 | Wang et al. |
| 2005/0033407 A1 | 2/2005 | Weber et al. |
| 2005/0049480 A1 | 3/2005 | Gray |
| 2005/0049481 A1 | 3/2005 | Gray et al. |
| 2005/0049482 A1 | 3/2005 | Gray et al. |
| 2005/0049683 A1 | 3/2005 | Gray et al. |
| 2005/0049684 A1 | 3/2005 | Gray et al. |
| 2005/0049685 A1 | 3/2005 | Gray et al. |
| 2005/0049686 A1 | 3/2005 | Gray et al. |
| 2005/0049688 A1 | 3/2005 | Gray et al. |
| 2005/0049689 A1 | 3/2005 | Gray et al. |
| 2005/0065430 A1 | 3/2005 | Wiethoff et al. |
| 2005/0065437 A1 | 3/2005 | Weber et al. |
| 2005/0079132 A1 | 4/2005 | Wang et al. |
| 2005/0080459 A1 | 4/2005 | Jacobson et al. |
| 2005/0085895 A1 | 4/2005 | Brown et al. |
| 2005/0090886 A1 | 4/2005 | MacDonald et al. |
| 2005/0107870 A1 | 5/2005 | Wang et al. |
| 2005/0113669 A1 | 5/2005 | Helfer et al. |
| 2005/0113676 A1 | 5/2005 | Weiner et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |

| | | | | | | |
|---|---|---|---|---|---|---|
| 2005/0131522 A1 | 6/2005 | Stinson et al. | | 2005/0182468 A1 | 8/2005 | Hunter et al. |
| 2005/0143651 A1 | 6/2005 | Verard et al. | | 2005/0182469 A1 | 8/2005 | Hunter et al. |
| 2005/0149002 A1 | 7/2005 | Wang et al. | | 2005/0183731 A1 | 8/2005 | Hunter et al. |
| 2005/0149157 A1 | 7/2005 | Hunter et al. | | 2005/0186239 A1 | 8/2005 | Hunter et al. |
| 2005/0149169 A1 | 7/2005 | Wang et al. | | 2005/0186244 A1 | 8/2005 | Hunter et al. |
| 2005/0152946 A1 | 7/2005 | Hunter et al. | | 2005/0186245 A1 | 8/2005 | Hunter et al. |
| 2005/0154374 A1 | 7/2005 | Hunter et al. | | 2005/0187140 A1 | 8/2005 | Hunter et al. |
| 2005/0155779 A1 | 7/2005 | Wang et al. | | 2005/0187582 A1 | 8/2005 | Weiner |
| 2005/0158356 A1 | 7/2005 | Hunter et al. | | 2005/0187600 A1 | 8/2005 | Hunter et al. |
| 2005/0159661 A1 | 7/2005 | Connelly et al. | | 2005/0192647 A1 | 9/2005 | Hunter et al. |
| 2005/0165470 A1 | 7/2005 | Weber | | 2005/0196421 A1 | 9/2005 | Hunter et al. |
| 2005/0165471 A1 | 7/2005 | Wang et al. | | 2005/0208095 A1 | 9/2005 | Hunter et al. |
| 2005/0169960 A1 | 8/2005 | Hunter et al. | | 2005/0209664 A1 | 9/2005 | Hunter et al. |
| 2005/0169961 A1 | 8/2005 | Hunter et al. | | 2005/0209665 A1 | 9/2005 | Hunter et al. |
| 2005/0175664 A1 | 8/2005 | Hunter et al. | | 2005/0209666 A1 | 9/2005 | Hunter et al. |
| 2005/0175665 A1 | 8/2005 | Hunter et al. | | 2005/0215764 A1 | 9/2005 | Tuszynski et al. |
| 2005/0175703 A1 | 8/2005 | Hunter et al. | | 2005/0216075 A1 | 9/2005 | Wang et al. |
| 2005/0178395 A1 | 8/2005 | Hunter et al. | | 2006/0287705 A1 | 12/2006 | Weber |
| 2005/0178396 A1 | 8/2005 | Hunter et al. | | | | |
| 2005/0178584 A1 | 8/2005 | Wang et al. | | | | |
| 2005/0181005 A1 | 8/2005 | Hunter et al. | | | | |

FOREIGN PATENT DOCUMENTS

| | | |
|---|---|---|
| WO | WO 99/42176 | 8/1999 |
| WO | WO 01/74241 | 10/2001 |
| WO | WO 02/094339 | 11/2002 |

| | | | |
|---|---|---|---|
| 2005/0181009 A1 | 8/2005 | Hunter et al. | |
| 2005/0181010 A1 | 8/2005 | Hunter et al. | |
| 2005/0182450 A1 | 8/2005 | Hunter et al. | |
| 2005/0182463 A1 | 8/2005 | Hunter et al. | |
| 2005/0182467 A1 | 8/2005 | Hunter et al. | |

* cited by examiner

RESONATOR WITH ADJUSTABLE CAPACITOR FOR MEDICAL DEVICE

CROSS REFERENCE TO RELATED APPLICATIONS

This application is a continuation of U.S. application Ser. No. 11/209,219, filed Aug. 23, 2005, the specification of which is incorporated herein by reference.

FIELD OF THE DISCLOSURE

The present disclosure relates generally to medical device apparatus, systems, and methods; and more particularly to medical device apparatus, systems, and methods for use during magnetic resonance imaging.

BACKGROUND

Stents and other metallic implants can cause artifacts in magnetic resonance (MR) images due in part to distortions in the magnetic field. Distortions in the magnetic field are often caused by the shape of the stent that acts to partially shield a radio frequency (RF) field generated during the MR procedure. This shielding of the RF field is known as the Faraday Effect and is caused by structures, such as stents, that have a "Faraday Cage" configuration.

Generally, a Faraday Cage configuration prevents an RF field from penetrating to the interior of such a structure. Because stents are not ideal but only partial Faraday cages, a small percentage of the RF field still is able to penetrate to the interior, however not enough to give a reasonable visibility in the stent interior.

One approach to achieving the reasonable visibility would be to raise the energy of the RF field to such high levels that enough energy remains after passing through the partial stent shield for visualization. Unfortunately, taking this approach will cause the tissue of the body to be heated to unacceptable levels.

BRIEF DESCRIPTION OF THE DRAWINGS

The illustrations provided in the Figures are not to scale.

DETAILED DESCRIPTION

Figure 1:
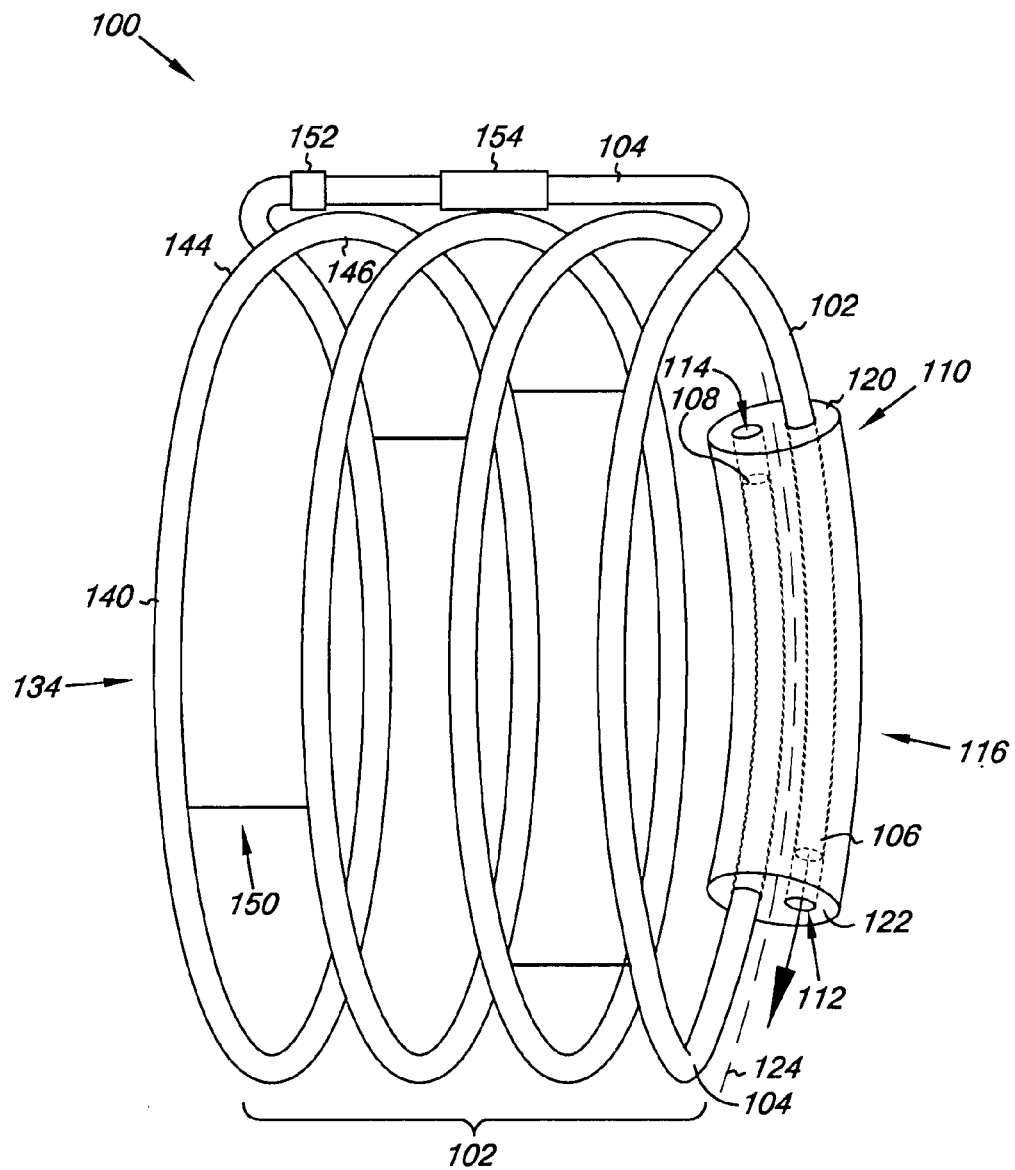
FIG. 1 illustrates an embodiment of a resonator device according to the present disclosure.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments. In addition, discussion of features and/or attributes for an element with respect to one figure can also apply to the element shown in one or more additional figures.

Embodiments of the present disclosure are directed to resonator devices, systems, and methods of using the resonator devices. Generally, a resonator device can be used in conjunction with an implantable medical device. These implantable medical devices include devices that traditionally have produced artifacts (signal loss) in images obtained by magnetic resonance imaging (MRI) systems. Embodiments of the present disclosure address the problem of artifacts (signal loss) produced in magnetic resonance (MR) images in addition to allowing for more complete MR images to be obtained from implantable medical devices.

Examples of such implantable medical devices include, but are not limited to, stents and/or shunts as are used in dialysis, artificial veins, arteries and grafts, esophageal stenosis, esophageal cancer, esophageal varacies, lung bronchi for cancer treatment, urethra, hydrocephalus shunt tubes, trachea, middle ear tubes, lymphatic ducts and grafts, gastrointestinal stenosis and inflammatory diseases (e.g. Crohn's disease), pyloric stenosis, implantable sensing devices, intravascular blood pressure devices, and biliary atresia. Examples of other types of implantable medical devices are also possible.

Typically, artifacts in MR images are due in large part to distortions in the magnetic field caused by the implanted medical device. For example, metallic stents can cause susceptibility and radiofrequency artifacts in MR images that do not allow for complete visualization of the stent lumen by magnetic resonance angiography (MRA). This is due to susceptibility artifacts and radiofrequency shielding of the metallic stents. Embodiments of the present disclosure can provide the potential for reduced artifacts during MR imaging with different MRA techniques through the use of a resonator device in conjunction with the medical device (e.g., metallic vascular stent). In addition, embodiments of the present disclosure also can provide for maintaining a resonance frequency of the resonator device by allowing changes in an inductance (L) of the resonator device to be proportionally offset by changes to a capacitance (C) of a capacitor of the resonator device so as to maintain the resonance frequency of the resonator device.

FIG. 1 illustrates one embodiment of a resonator device 100 of the present disclosure. The resonator device 100 is illustrated as having an inductor coil 102 and a conductive member 104 that extends from the inductor coil 102. In the present embodiment, the inductor coil 102 and the conductive member 104 are in the form of an electrically conductive body having a first end 106 and a second end 108. As illustrated, the conductive member 104 can be positioned adjacent to and extend over the inductor coil 102.

In the present embodiment, the resonator device 100 further includes a sleeve 110. In one embodiment, the sleeve 110 includes surfaces defining a first socket 112 and a second socket 114. In addition, the sleeve 110 can include a dielectric material positioned between at least the first and second sockets 112, 114. In one embodiment, the sleeve 110 can be completely formed of the dielectric material. In an alternative embodiment, the dielectric material can form at least a portion of and be located between the sockets 112, 114, while the remainder of the sleeve 110 is formed from a material that is different than the dielectric material.

The first and second sockets 112, 114 can receive at least a portion of the inductor coil 102 and the conductive member 104, respectively, to form a capacitor structure 116. For example, the first end 106 of the inductor coil 102 can pass into the first socket 112 and the second end 108 of the conductor member 104 can pass into the second socket 114 adjacent the first end 106 to form the capacitor structure 116. As a result, the induction coil 102 and the conductive member 104 can be electrically connected in series through the capacitor structure 116 to form the resonator device 100.

The resonator device 100 can be configured with a resonance frequency (F) that can be matched to the Larmor frequency of the MRI system (e.g., 64 Mz at 1.5 T). The resonance frequency (F) is given by the inverse square root of the product LC (inductance (L) times (×) capacitance (C)):

$$F = 1/(2 \cdot (\pi) \cdot (L \cdot C)^{0.5})$$

The inductance (L) value is a function of, besides other things, the cross sectional area defined by the induction coil 102. The capacitance value (C) is a function of, besides other things, the surface area of the conducting electrodes, the distance between the electrodes and the dielectric substance that separates the electrodes. As discussed herein, the cross sectional area defined by the induction coil 102 can change as the inductor coil 102 gets larger or smaller (e.g., as the circumference of the induction coil changes). As this happens, the relative position of the electrodes (i.e., the inductor coil and/or the conductive member inside the sockets 112, 114, respectively) change as discussed herein. If the capacitance (C) value were to stay the same while the inductance (L) value changes, the resonance frequency (F) value may no longer be matched to the Larmor frequency.

Embodiments of the present disclosure, however, allow the resonance frequency (F) of the resonator device 100 to continue to be matched to the Larmor frequency of the MRI system due to predetermined changes in the capacitance (C) value that correspond to and compensate for changes in the inductance (L) value as the cross-sectional area of the induction coil 102 changes. In other words, embodiments of the present invention allow for maintaining the resonance frequency of the resonator device 100 as the circumference of the induction coil 102 changes. As discussed, changes in the circumference of the inductor coil 102 of the resonator device 100 cause changes in the inductance (L) of the resonator device 100. The present disclosure allows for proportional changes to the capacitance (C) value of the capacitor 116 of the resonator device 100 as the circumference of the induction coil 102 changes to maintain the resonance frequency of the resonator device 100.

For example, proportionally changing the capacitance of the capacitor structure 116 of the resonator device 100 as the circumference of the induction coil 102 changes can include increasing the circumference of the inductor coil 102 and proportionally decreasing the capacitance value (C) of the capacitor structure 116 as the circumference increases. In addition, proportionally changing the capacitance value (C) of the capacitor structure 116 of the resonator device 100 can include changing a position of a portion of the inductor coil 102 adjacent the dielectric material of the sleeve 110 relative a portion of a conductive member 104 that couples the resonator device 100 in series. In one embodiment, proportionally changing the capacitance value (C) of the capacitor structure 116 of the resonator device 100 can include changing the capacitance value (C) based on a linear function. In addition, proportionally changing the capacitance value (C) of the capacitor structure 116 can include tapering at least a portion of a dielectric material of the sleeve 110 of the capacitor structure 116 across which at least one electrodes of the capacitor pass.

As illustrated, the first end 106 of the induction coil 102 can be positioned within the first socket 112, and the second end 108 of the conductive member 104 can be positioned within the second socket 114. In one embodiment, both the first and second ends 106, 108 can travel within the respective first and second sockets 112, 114. In other words, portions of the induction coil 102 and the conductive member 104 that extend from the first and second ends 106, 108 can move within the sockets 112, 114 as the cross-sectional area defined by the induction coil 102 changes. In an alternative embodiment, one of the first end 106 of the inductor coil 102 or the second end 108 of the conductive member 104 can remain static relative the sleeve 110, while the other end (i.e., the first end 106 of the induction coil 102 or the second end 108 of the conductive member 104) can travel within the respective socket 112, 114. In one embodiment, changes in the cross-sectional area defined by the induction coil 102 can occur during deployment of the resonator device 100, as discussed herein.

In forming the capacitor structure 116, portions of the induction coil 102 and the conductive member 104 can form the electrodes of the capacitor 116. These electrodes can be formed from portions of the induction coil 102 and the conductive member 104 that extend from the first and second ends 106, 108, respectively. As discussed herein, because the one or both of the portions of the induction coil 102 and the conductive member 104 that form the electrodes can travel within the sockets 112, 114, the capacitance value (C) of the capacitor structure 116 can be changed.

As illustrated, the first socket 112 extends from a first end 120 of the sleeve 110 and the second socket 114 extends from a second end 122 of the sleeve 110. The cross-sectional area and shape of the sockets 112, 114 and the portions of the induction coil 102 and the conductive member 104 can be configured to allow the portions of the induction coil 102 and the conductive member 104 forming the electrodes to contact the dielectric material of the sleeve 110. As will be appreciated, the cross-sectional shape can have a number of different configurations. For example, the shape of the portions of the induction coil 102 and conductive member 104 forming the electrodes can be circular, oval, rectangular, polygonal, concave, and convex. Other cross-sectional shapes are also possible. As will be appreciated, the sockets 112, 114 can also have the corresponding shape so as to receive and allow the electrodes to pass within the sockets 112, 114.

As appreciated, the capacitance value (C) for the capacitor structure 116 is proportional to the surface area of the induction coil 102 and the conductive member 104 that act as the electrodes of the capacitor structure 116. So, as the length of the induction coil 102 and/or the conductive member 104 that extend into the sockets 112, 114 changes so does the capacitance value (C). As discussed herein, the length that the induction coil 102 and/or the conductive member 104 that extend into the sockets 112, 114 can change as the cross-sectional area defined by the induction coil 102 changes.

For example, as the circumference of the induction coil 102 changes from a first size to a second size that is larger than the first size, at least one of the first end 106 and/or the second end 108 move within the first socket 112 and the second socket 114 of the sleeve 110 of dielectric material. So, the first end 106 and the second end 108 can be in a first position when the induction coil 102 has a first circumference and in a second position when the induction coil 102 has a second circumference that is greater than the first circumference. As a result, the capacitance value (C) of the capacitor structure 116 changes from a first value when the first end 106 and the second end 108 are in the first position and to a second valve different than the first value when at least one of the first end 106 and the second end 108 move in the socket 112, 114 to the second position.

In one embodiment, these changes in the capacitance (C) can compensate for changes in the cross-sectional area defined by the inductor coil 102. For example, such configurations can include, but are not limited to, the dielectric material between the sockets 112, 114 having two or more sections that each has a dielectric constant that is different than the dielectric constant of other sections of the dielectric layer. This configuration can provide for a change in the capacitance value (C) of the capacitor structure 108 between a first end 120 and the second end 122 of the sleeve 110. For example, the value of the dielectric constant for the two or more sections can increase between the first end 120 and the second end 122 of the sleeve 110 to change the capacitance value of the capacitor structure 116. Alternatively, the value of the dielectric constant for the two or more sections can decrease between the first end 120 and the second end 122 of the sleeve 110 to change the capacitance value of the capacitor structure 116.

Figure 2:
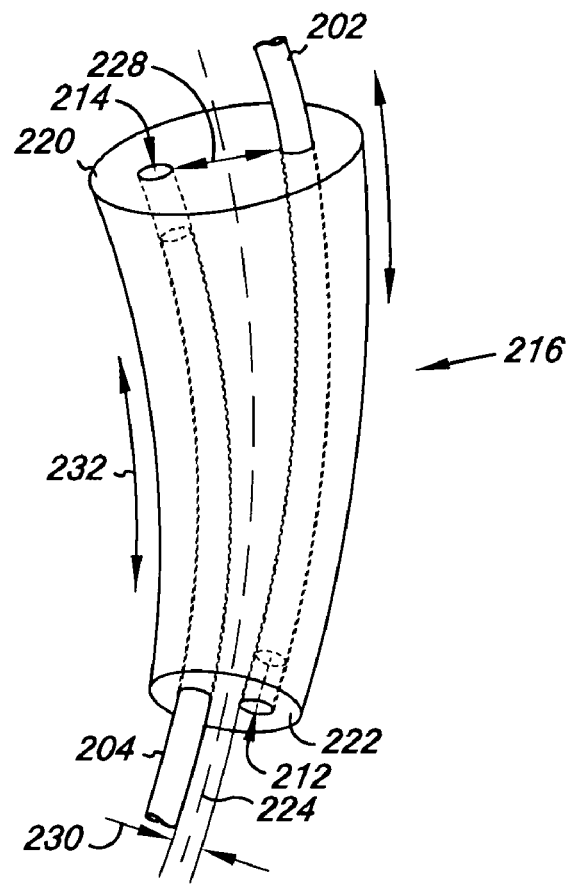
FIG. 2 illustrates an embodiment of an adjustable capacitor structure of the resonator device according to the present disclosure.

The capacitance value (C) is also inversely proportional to the distance between the electrodes. FIG. 2 illustrates an additional embodiment of the capacitor structure 216 for use with the resonator device that utilizes this aspect of the capacitor structure. According to the present disclosure the distance between the first socket 212 and the second socket 214 adjacent the first end 220 can be greater than the distance between the first socket 212 and the second socket 214 adjacent the second end 222. In one embodiment, the dielectric material between the first and second sockets 212, 214 tapers between the first end 220 of the sleeve 210 and the second end 222 of the sleeve 210. As the distance between the electrode changes, so does the thickness of the dielectric layer and, as a result, the capacitance value (C) of the capacitor structure 216. In addition, an exterior surface 226 of the sleeve 210 can also tapers between the first end 220 and the second end 222.

Embodiments of the present disclosure allow for the distance between the first socket 212 and the second socket 214 taken perpendicular to a longitudinal axis 224 of the sleeve 210 to change in a predetermined fashion between the first end 220 and the second end 222 of the sleeve 210. In one embodiment, the predetermined fashion can be expressed as a linear function:

$$d_1 = \alpha l + d_2$$

where $d_1$ is the distance 228 between the first socket 212 and the second socket 214 adjacent the first end 220, $d_2$ is the distance 230 between the first socket 212 and the second socket 214 adjacent the second end 222, l is a distance 232 that at least one of the first end 206 and the second end 208 move within the first socket 212 and the second socket 214 of the sleeve 110 of dielectric material, and α is a rate of change along the longitudinal axis 224 of the sleeve 210. As appreciated, the values selected for the distance variables $d_1$, $d_2$, l, and rate of change variable α can be determined based at least in part on one or more of the dielectric constant of the dielectric being used for the capacitor structure 216, the size of the capacitor structure 216, and the size of the induction coil 202 in its undeployed state and a deployed state, among other factors.

Referring again to FIG. 1, the induction coil 102 includes an elongate configuration having windings that extend circumferentially in a helical structure as illustrated. In one embodiment, windings of the helical structure can be equally spaced from each other. In an alternative embodiment, windings of the helical structure can have a predetermined non-consistent spacing relative to each other along the helical structure. In one embodiment, this non-consistent spacing can allow for differences in the winding density (number of windings per meter) along the length of the induction coil 102.

In one embodiment, the induction coil 102 can extend continuously down the length of the resonator device 100 (i.e., the induction coil 102 does not deviate along the length of the resonator device 100). Alternatively, the induction coil 102 can include a "zigzag" configuration as the induction coil 102 extends down the length of resonator device 100. As will be appreciated, other shapes and configurations that can act as an induction coil, besides helical coils, are also possible.

The induction coil 102 can be formed of one or more conductive members (e.g., two or more members in parallel). In addition, different cross-sectional geometries can be used for the induction coil 102. For example, the cross-sectional geometries can include circular rectangular, oval and/or polygonal, among others. Other shapes are also possible.

The conductive members of the induction coil 102 can also have a number of different sizes and structural configurations. For example, the conductive members can have a size and a shape sufficient to maintain a predetermined shape of the induction coil 102 in its deployed state. Alternatively, the size and the shape of each of the induction coil 102 can be supported by a structural support, as discussed in co-pending U.S. patent application entitled "Resonator for Medical Device", U.S. patent application Ser. No. 11/207,304, can be configured to maintain the predetermined shape of the induction coil 102 in its deployed state.

As will be appreciated, parameters of the induction coil 102 and the capacitor structure 116 can be used to tune the resonator device 100 to a predetermined radio frequency (RF). Examples of parameters used in tuning the resonator device 100 include, but are not limited to, the number of turns and the cross sectional area of the inductor coil 102 of the resonator device 100.

The configuration of the capacitor structure 116 can also be modified in tuning the resonator device 100. Predetermined modifications to the size, shape, distance between the capacitor plates and dielectric material configuration, for example, can allow for adjustments to be made in the tuning of the resonator device 100.

The induction coil 102 is configured to allow the lumen 134 of the resonator device 100 to expand from a first cross-sectional size in an un-deployed state to a second cross-sectional size in a deployed state. This allows the resonator device 100 to be introduced into a body with the first cross-sectional size and then be expanded to the second cross-sectional size at the predetermined location within the body. For example, the resonator device 100 can be positioned over a balloon of a balloon catheter in its first cross-sectional size (e.g., its un-deployed configuration). In one embodiment, there can be a frictional fit between the lumen of the sleeve 110 and one or both of the induction coil 102 and the conductive member 104 that are each positioned in the lumen of the sleeve 110. This configuration can allow the resonator device 100 to be better secured to the balloon in the un-deployed configuration and to better maintain its shape once deployed. The balloon can then be inflated to expand the resonator device 100 to its second cross-sectional size (e.g., its deployed configuration). Alternatively, when the induction coil 102 is formed of a memory metal alloy (such as Nitinol), the resonator device 100 can be introduced into the body in its first cross-sectional size (e.g., its un-deployed configuration) and then released to expand the resonator device 100 to its second cross-sectional size (e.g., its deployed configuration).

In one embodiment, the circumference of lumen 134 can be essentially equal along the length of the resonator device 100. In an alternative embodiment, the expandable circumference of the lumen 134 can change along the length of the resonator device 100. For example, the circumference of the lumen 134 can increase or decrease along the length of the resonator device 100. Alternatively, the circumference of the lumen 134 can increase along the length of the resonator device 100 to a predetermined point and then decrease again. Other configurations are also possible.

Possible dielectric materials include, but are not limited to, metal oxides such as tantalum oxide, aluminum oxide, niobium oxide, niobium-zirconium alloy oxide; ceramic and/or glasses such as alumina or aluminosilicates and borosilicate; minerals such as mica (an alkali metal aluminosilicate, hydrate). In an additional embodiment, the sleeve 110 of the dielectric material can be formed of a flexible polymeric material so as to allow the sleeve 110 to bend as the resonator device 100 moves between the un-deployed state and the deployed state, as discussed herein. Examples, include, but are not limited to, polymers such as polyesters (e.g., Mylar), polyamides (e.g., Nylon), polycarbonate, polyetheretherketones (PEEK), poly(phenylene oxide), poly(phenylene sulfide), poly(vinyl chloride), poly(chlorotrifluoroethylene), poly(p-phenyleneethylene), polystyrene, polyethylene, polypropylene, and poly(tetrafluoroethylene). Other dielectric materials are also possible.

As will be appreciated, the sleeve 110 can be formed through any number of techniques. For example, the sleeve 110 could be formed through a molding process and/or a number of different surface coating techniques. Examples of such coating techniques include, but are not limited to, chemical or physical deposition techniques. Example of these respective techniques include, but are not limited to, solution casting, ink-jet deposition, aerosol deposition, dip coating, spin coating, plasma polymerization, electrochemical polymerization, catalytic polymerization, photo-activatable polymerization, molecular-aggregation, vacuum sublimation, plasma deposition, pulse-laser deposition (PLD), matrix assisted pulsed-laser evaporation, chemical vapor deposition (CVD), plasma assisted CVD, thin film growth, sputtering, evaporation (thermal and e-beam), ion vapor deposition, and laser and/or electron beam assisted processing (e.g., laser ablation processing).

As illustrated in the present embodiment, the induction coil 102 can be formed from elongate member 140 that extends at least partially between the first and second end 106 and 108. The elongate member 140 also includes a surface defining at least a portion of the lumen 134 of the resonator device 100. In one embodiment, the elongate member 140 can be formed of a material which is electrically conductive. In addition, the material of the elongate member 140 also has the requisite strength and elasticity characteristics to permit the induction coil 102 to be expanded from the first cross-sectional size to the second cross-sectional size. The material also allows the induction coil 102 to retain its expanded configuration with the second cross-sectional size.

In one embodiment, the elongate member 140 of the induction coil 102 can be a metal or metal alloy. Examples of such metals and metal alloys include, but are not limited to, platinum, magnesium, tungsten, titanium, tantalum, niobium, and memory metals alloys such as Nitinol, titanium-palladium-nickel, nickel-titanium-copper, gold-cadmium, iron-zinc-copper-aluminum, titanium-niobium-aluminum, hafnium-titanium-nickel, iron-manganese-silicon, nickel-titanium, nickel-iron-zinc-aluminum, copper-aluminum-iron, titanium-niobium, zirconium-copper-zinc, and nickel-zirconium-titanium. Other metal and metal alloys are also possible, including those having suitable plastic materials having the requisite characteristics described herein. Further examples include polymeric wires provided with noble metal (e.g., gold) sputter coat, such as polyamide 12, polyethylene, and polycarbonate sputter coated with gold.

The elongate member 140 can have a cylindrical cross-section, but as will be appreciated the elongate member 140 could have other cross-sectional configurations, such as triangular, square, rectangular, and/or hexagonal, among others. In addition, the elongate member 140 can have a non-uniform cross-sectional configuration along its length, such as tapered, bell shaped, or changing from one cross-sectional shape (e.g., cylindrical) to a second cross-sectional shape (e.g., elliptical) in case of a bifurcation.

As illustrated, the elongate member 140 can be configured as a continuous winding of connected spirals or loops having a sinuous or zigzag configuration. As used herein, a winding includes one or more electrically conductive wires wound one complete turn about a center of the resonator device 100. The elongate member 140 can also be fixedly secured to one another at predetermined intersection points and connectors so as to help resist radial collapse of the inductor coil 102 and to help maintain its second cross-sectional size.

In one embodiment, the connection member 104 can extend over the induction coil 102 either adjacent an exterior surface 144 or an interior surface 146 of the induction coil 102. As illustrated, the connection member 104 can be an elongate member that passes adjacent the exterior surface 144 of the induction coil 102. The capacitor structure 116, the conductive member 104 and/or the induction coil 102 can also be coated with an electrical insulator (e.g., e-PTFE or pyrolene) to electrically insulate the structures of the resonator device 100.

In one embodiment, the connection member 104 can be constructed of the same material as the induction coil 102. Alternatively, the connection member 104 can be constructed of a material that is different (e.g., different conductivity, flexibility, malleability, stiffness) than the material used for the induction coil 102. In addition, the connection member 104 can have a number of different cross-sectional profiles, including but not limited to, circular, oval, triangular, and polygonal. The cross-sectional area of the connection member 104 can also be greater than or equal to that of the induction coil 102. For example, the connection member 104 could have a circumference that is greater than or equal to the circumference of the induction coil 102. In an alternative embodiment, the cross-sectional area of the connection member 104 can be less than or equal to that of the induction coil 102.

In various embodiments, the induction coil 102 and the connection member 104 can be formed from a single piece of material. For example, the induction coil 102 and the connection member 104 could be cut (laser or water cut) from a single elongate tube of material. Alternatively, the induction coil 102 and the connection member 104 could be formed from a single length of material (e.g., a length of wire). The first end 106 of the induction coil 102 and the second end of the connection member 104 could then be introduced and passed into the first and second sockets 112, 114 of the sleeve 110 to provide the capacitor structure 116.

In an alternative embodiment, the induction coil 102 and the connection member 104 can be formed from either a single piece of material or a single length of material, as discussed herein. For example, in one configuration a single piece or length of material can be used to form the induction coil 102 and the connection member 104. From this configuration, the connection member 104 would then be bent back over the windings of the induction coil 102 to position the second end of the connection member 104 adjacent the second end of the induction coil 102. The first and second ends 106, 108 can then be positioned within the sockets 112, 114 of the sleeve 110 across the dielectric material to complete the circuit of the resonator device 100.

In addition, one or more of the components of the resonator device 100 can be made radioopaque. For example, one or more portions of the induction coil 102 could be clad with a radioopaque material to make the resonator device 100 radioopaque. Alternatively, one or more discrete radioopaque markers having a predetermined shape can be added to predetermined portions of the resonator device 100. Example of suitable materials for the radioopaque markers include, but are not limited to, copper, tungsten, gold, silver, platinum and alloys thereof.

The induction coil 102 can further include spacers 150 positioned between the windings of the induction coils 102. In one embodiment, the spacers 150 provide for electrical insulation, structural support, and structural spacing for adjacent windings of the coil 102. Spacers 150 can be coupled to the induction coil 102 in a number of ways. For example, a pair of spacers 150 could be sandwiched around the induction coil 102 and bonded with heat and/or chemical adhesive. Spacers 150 could be wound, twisted and/or braided around each other and the induction coil 102. The spacers 150 could then be bonded with heat and/or chemical adhesive.

Examples of suitable materials for the spacers 150 include, but are not limited to non-biodegradable and/or biodegradable materials. Examples of non-biodegradable materials include, but are not limited to, ceramic, polystyrene; polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL); squalene emulsions; and mixtures and copolymers of any of the foregoing.

Examples of biodegradable materials include, but are not limited to, polycarboxylic acid, polylactic acid, polyhydroxybuterate, polyanhydrides including maleic anhydride polymers; polyorthoesters; poly-amino acids; polyethylene oxide; polyphosphazenes; polyactic acid, polyglycolic acid and copolymers and copolymers and mixtures thereof such as poly(L-lactic acid) (PLLA), poly(D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocaronates, and polydimethyltrimethylcarbonates; cyanoacrylate; calcium phosphates; polyglycosaminoglycans; macromolecules such as polysaccharides (including hyaluronic acid, cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

The spacers 150 can further include one or more therapeutic agents. In one embodiment, the one or more therapeutic agents can be integrated into the material matrix of and/or coated on the surface of the spacers 150. The one or more therapeutic agents can then leach and/or be released from the spacers 150 once implanted.

Examples of therapeutic agents include, but are not limited to, pharmaceutically acceptable agents such as non-genetic therapeutic agents, a biomolecule, a small molecule, or cells. Exemplary non-genetic therapeutic agents include anti-thrombogenic agents such as heparin, heparin derivatives, prostaglandin (including micellar prostaglandin E1), urokinase, and PPack (dextrophyenylalanine proline arginine chloromethylketone); anti-proliferative agents such as enoxaprin, angiopenptin, sirolimus (rapamycin), tacrolimus, everolimus monoclonal antibodies capable of blocking smooth muscle cell proliferation, hirudin, and acetylsalicylic acid; anti-inflammatory agents such as dexamethasone, rosiglitazone, prenisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof; antibiotics such as gentamycin rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; and any combinations and prodrugs of the above.

Exemplary biomolecules includes peptides, polypeptides and proteins; oligonucleotides; nucleic acids such as double or single stranded DNA (including naked and cDNA), RNA, antisense nucleic acids such as antisense DNA and RNA, small interfering RNA (siRNA), and riobozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-linear example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin-) cells including Lin-CD34−, Lin-CD34+, Lin-cKit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

The therapeutic agents may be combined to the extent such combination is biologically compatible.

Figure 3:
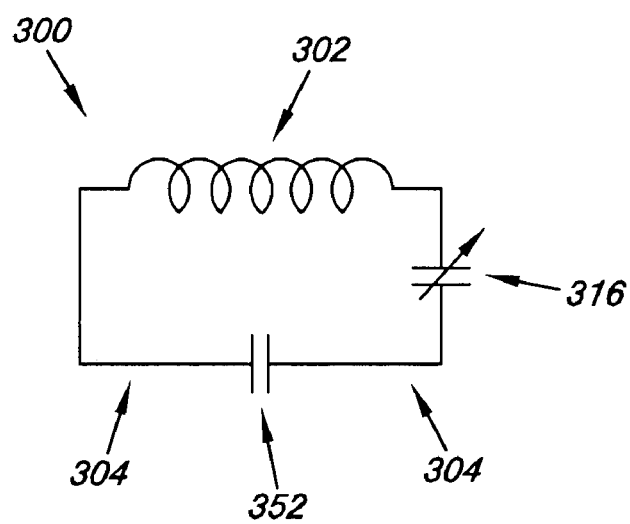
FIG. 3 illustrates an embodiment of a circuit schematic representative of the resonator device according to the present disclosure.

The resonator device 100 of the present disclosure can also include a second capacitor 152 in series between the first end 106 of the inductor coil 102 and the second end 108 of the conductive member 104. By way of illustration, FIG. 3 provides a circuit diagram of the resonator device 300 that includes the induction coil 302, the conductive member 304, the capacitor structure 316, and the second capacitor 352.

Referring again to the embodiment illustrated in FIG. 1, the second capacitor 152 can have a predetermined fixed capacitance value that is selected so as to allow adjustments in the tuning of the resonator device 100 to be accommodated with the capacitor structure 116, as discussed herein. In other words, the predetermined fixed capacitance value of the second capacitor 152 can be selected to provide a resonance frequency (F) matched to the Larmor frequency of the MRI system when the resonator device 100 is in un-deployed state, where the capacitor structure 116 compensates for changes in the cross sectional area defined by the induction coil 102 as the resonator device 100 is deployed. This can allow the resonance frequency of the resonator device 100 to better match the Larmor frequency of the MRI system as the device 100 is deployed.

In an additional embodiment, the resonator device 100 can further include a resistor 154 coupled in series with the induction coil 102, the conductive member 104, the second capacitor 152, and the capacitor structure 116. In one embodiment, the use of a resistor in the resonator device 100 allows for an inductive response across a wider spectrum of RF energies as compared to devices without such a resistor 154. Other configurations are also possible.

As will be appreciated, the present embodiment allows the resonator device described herein to be used in conjunction with a stent that may or may not already be implanted into the body. For example, the resonator device could be implanted adjacent the stent that is already in position within a patient. Alternatively, the resonator device could be positioned relative the stent prior to its implantation. The devices could then be implanted together, although not necessarily at the exact same time. Examples of such configurations are discussed herein.

Figure 4:
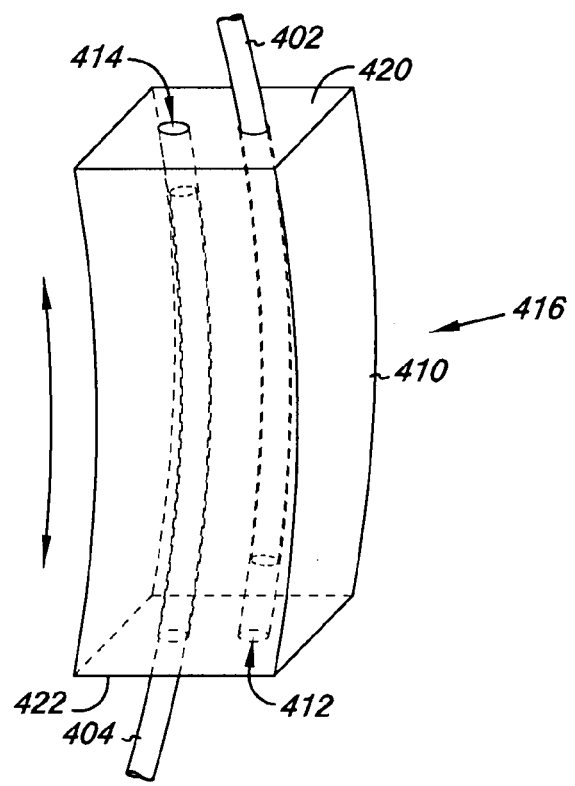
FIG. 4 illustrates an embodiment of the adjustable capacitor structure of the resonator device according to the present disclosure.
Figure 5:
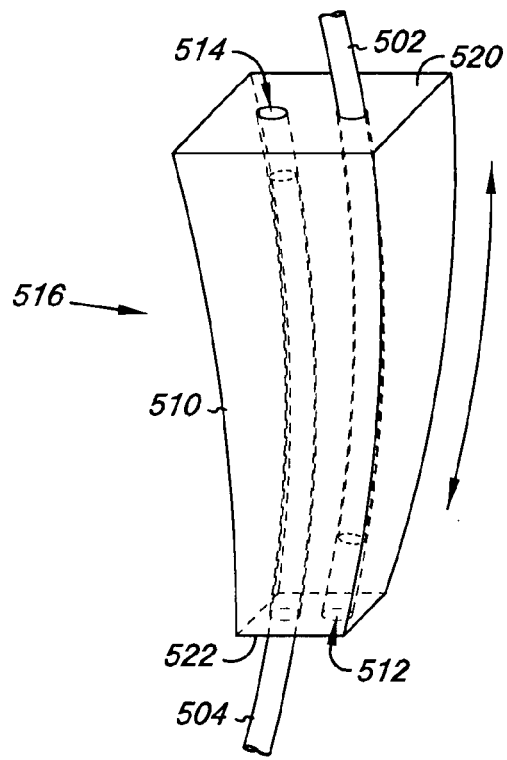
FIG. 5 illustrates an embodiment of the adjustable capacitor structure of the resonator device according to the present disclosure.

FIG. 4 provides an additional embodiment of the capacitor structure 416 according to the present disclosure. As illustrated, the sleeve 410 has a polygonal cross-sectional shape. FIG. 5 provides an additional embodiment in which the sleeve 510 having a polygonal cross-sectional shape includes a distance between the first and second sockets 512, 514 that tapers between the first and second end 520, 522 of the sleeve 510.

Figure 6:
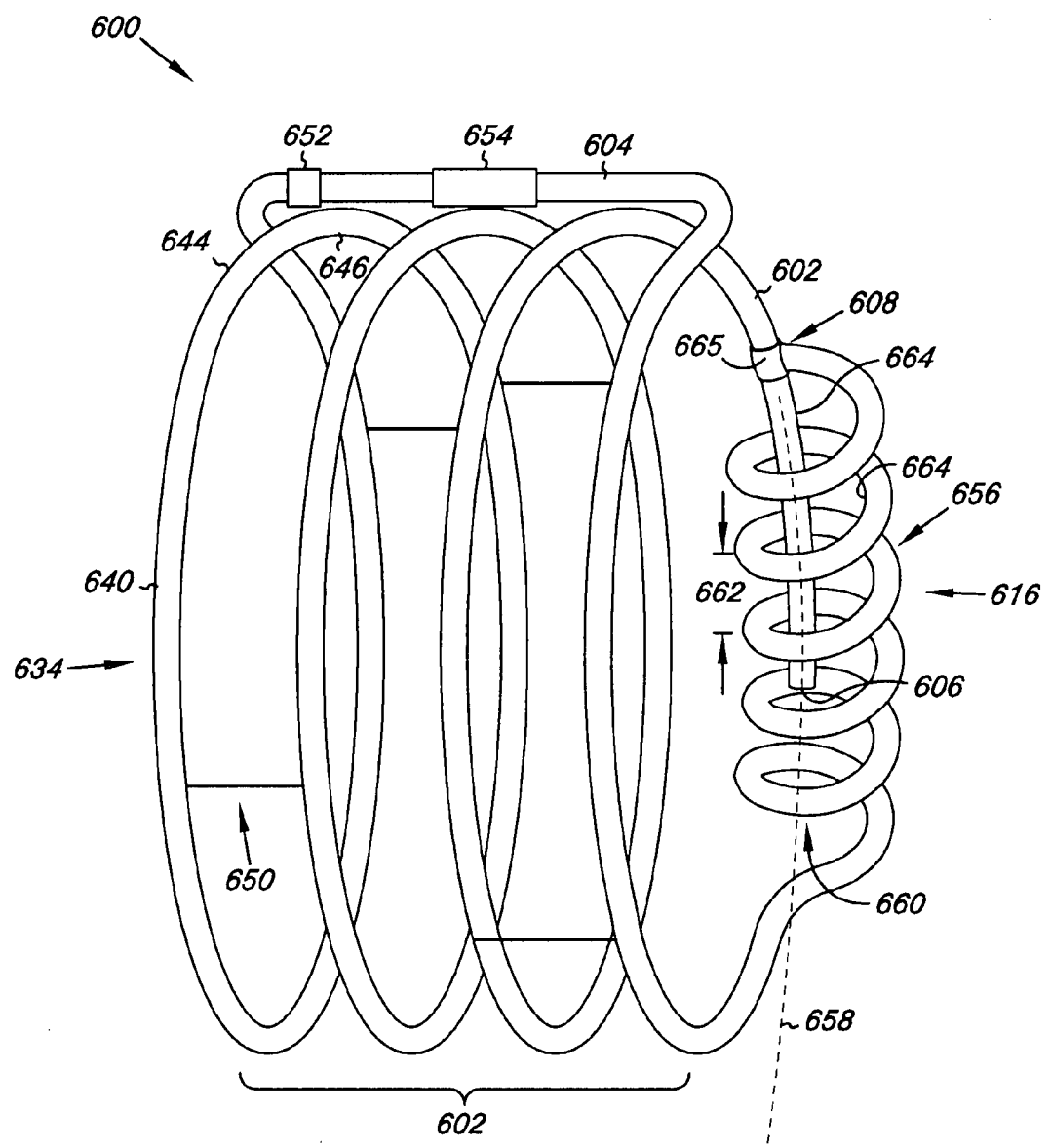
FIG. 6 illustrates an embodiment of a resonator device according to the present disclosure.

FIG. 6 provides an illustration of an additional embodiment of a resonator device 600 of the present disclosure. The resonator device 600 includes, besides other things, the induction coil 602, and conductive member 604, as discussed herein. The resonator device 600 also includes a portion of the conductive member 604 configured as a spiral 656 extending along a longitudinal axis 658. As illustrated, the conductive member 604 forming the spiral 656 defines a passage 660 through which at least a portion of the induction coil 602 can pass.

As will be appreciated, the conductive member 604 forming the spiral 656 can have a variety of coil densities (e.g., turns/distance). For example, the coil density can be such that the surfaces of adjacent turns of the conductive member 604 are in contact. Alternatively, the coil density can be such that a gap 662 exists between the adjacent turns of the conductive member 604 along the spiral 656.

In addition, the size of the gap 662 between the adjacent turns of the conductive member 604 can be uniform and/or non-uniform. For example, FIG. 6 illustrates the gap 662 having an essentially uniform size between the adjacent turns of the conductive member 604 along the spiral 656. Alternatively, the size of the gap 662 between adjacent turns of the conductive member 604 can change along the length of the spiral 656. For example, the size of the gap 662 between adjacent turns of the conductive member 604 can decrease along the longitudinal axis 658 of the spiral 656. Other configurations for the size of the gap 662 are also possible.

As illustrated, at least a portion of the induction coil 602 passes through the passage 660 to form the capacitor structure 616. For example, the portion of the induction coil 602 that passes into the passage 660 and the conductive member 604 forming the spiral 656 can include a dielectric layer 664 between the structures to form the capacitor structure 616. In one embodiment, one or both of the induction coil 602 that passes into the passage 660 and/or the conductive member 604 forming the spiral 656 can have a dielectric layer. Alternatively, a sleeve of dielectric material can be positioned between the induction coil 602 that passes into the passage 660 and/or the conductive member 604 forming the spiral 656.

As discussed herein, the thickness and/or changes in the dielectric material along either the conductive member 604 forming the spiral 656 and/or the induction coil 602 that passes into the passage 660 can be used to change the capacitance (C) so as to compensate for changes in the cross-sectional area defined by the inductor coil 602. In addition, the conductive member 604 forming the spiral 656 can taper so as to allow changes in the distance between the induction coil 602 that passes into the passage 660 and the conductive member 604 defining the passage. As discussed herein, these changes in distance between the electrodes of the capacitor structure 616 allow for changes in the capacitance value (C) of the capacitor structure 616.

The embodiment of the resonator device 600 further includes a guide collar 665 that extends from the conductive member 604 forming the spiral 656. In one embodiment, the guide collar 665 allow the induction coil 602 to pass there through so as to help maintain the relative position of the induction coil 602 that passes into the passage 660. In alternative embodiment, the resonator device 600 does not include the guide collar 665.

Examples of suitable dielectric materials and techniques for forming the dielectric layer 664 are as discussed herein. In addition, it is possible to use a method of polyelectrolyte layer deposition to achieve the dielectric layer 664 of suitable shape and thickness on one or both of the conductive member 604 forming the spiral 656 and/or the induction coil 602 that passes into the passage 660. For example, it is possible to sequentially absorb poly(acrylic acid) (PAA) and poly(allylamine hydrochloride) (PAH) on the conductive member 604 and/or the induction coil 602 that form the capacitor structure 616. The PAA-PAH layers can then undergo heat induced amidation at 215° C. for 30 minutes to create a nylon dielectric layer (e.g., 50 nanometer).

Figure 7:
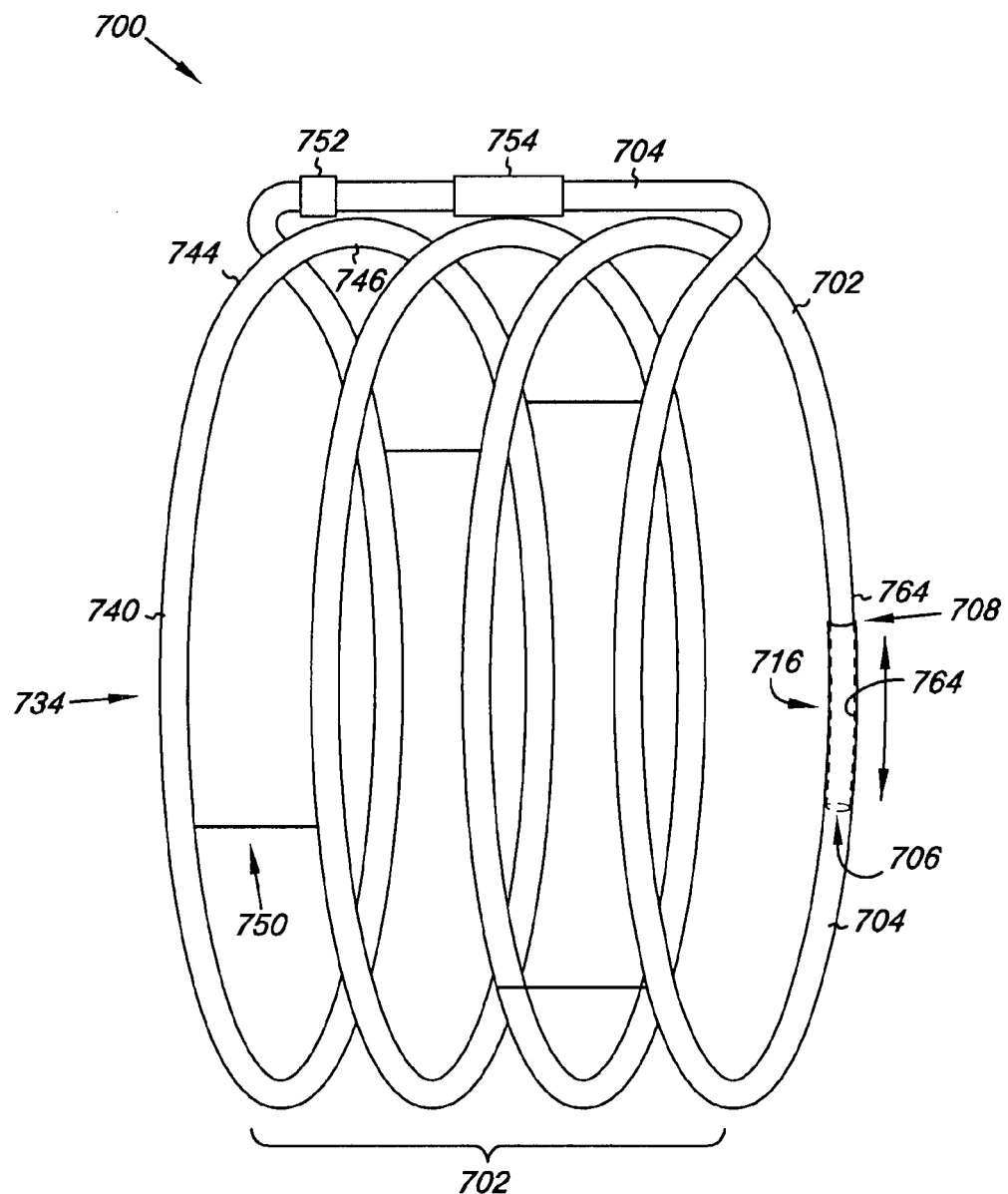
FIG. 7 illustrates an embodiment of a resonator device according to the present disclosure.

FIG. 7 provides an illustration of an additional embodiment of a resonator device 700 of the present disclosure. The resonator device 700 includes, besides other things, the induction coil 702, and conductive member 704. In the present embodiment, a surface of the conductive member 704 defines a socket 768 into which a portion of the induction coil 702 can pass.

As illustrated, at least a portion of the induction coil 702 passes into the socket 768 to form the capacitor structure 716. For example, the portion of the induction coil 702 that passes into the socket 768 defined by the conductive member 604 can include a dielectric layer 764 between the structures to form the capacitor structure 716. In one embodiment, one or both of the induction coil 702 that passes into the socket 768 and/or the surface of the conductive member 704 defining the socket 768 can have a dielectric layer. Alternatively, a sleeve of dielectric material can be positioned between the induction coil 702 that passes into the socket 768 and/or the conductive member 704 forming the socket 768.

As discussed herein, the thickness and/or changes in the dielectric material along either the conductive member 704 forming the socket 768 and/or the induction coil 702 that passes into the socket 768 can be used to change the capacitance (C) so as to compensate for changes in the cross-sectional area defined by the inductor coil 702. As discussed herein, these changes in dielectric material and/or the distance between the electrodes of the capacitor structure 716 allow for changes in the capacitance value (C) of the capacitor structure 716. Examples of suitable dielectric materials and techniques for forming the dielectric layer 764 are as discussed herein.

Figure 8:
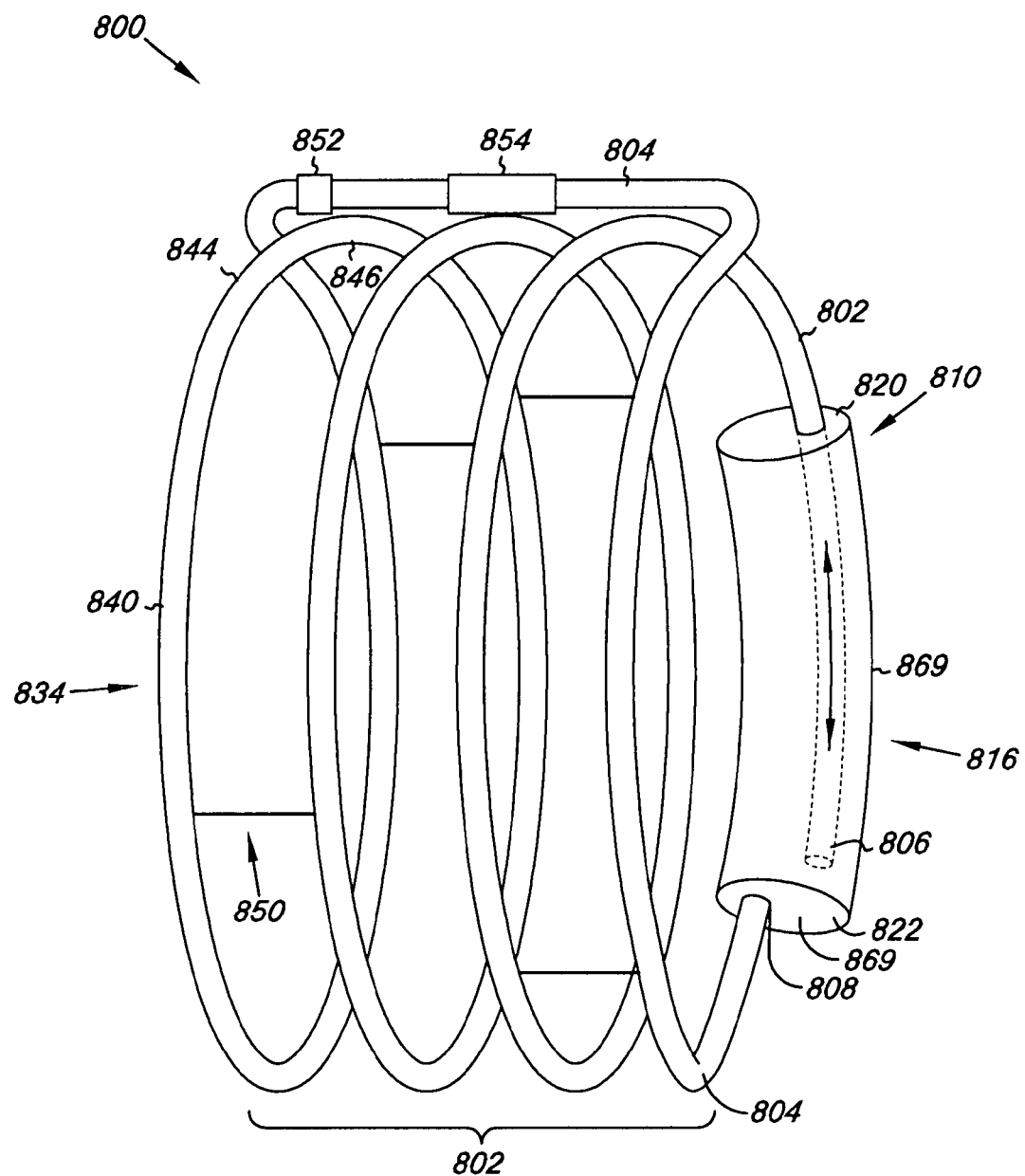
FIG. 8 illustrates an embodiment of a resonator device according to the present disclosure.

FIG. 8 illustrates an additional embodiment of the resonator device 800 of the present disclosure. The resonator device 800 is illustrated as having the inductor coil 802 and the conductive member 804, as discussed herein. The resonator device 800 also includes sleeve 810. In one embodiment, the sleeve 810 includes surfaces defining either the first socket or the second socket, as discussed herein.

As illustrated, the sleeve 810 includes the first socket 812 that receives the inductor coil 802, as discussed herein. In addition, the resonator device 800 includes a conductive layer 869 that at least partially covers, or coats, the sleeve 810. For example, the conductive layer 869 can covers the sleeve 810 between the first and second ends 820 and 822, including the second end 822. In other words, the conductive layer 869 covers the sleeve 810 except for the surface that defines the first end 820 of the sleeve 810 and across which the first socket 812 receives the inductor coil 802.

In the present embodiment, the conductive member 804 can be electrically coupled to the conductive layer 869, for example, at or about the second end 822 of the sleeve. The dielectric material positioned between the inductor coil 802 and the conductive layer 869 form the capacitor structure 816. In one embodiment, positioning the conductive layer 869 on the sleeve 810 helps to provide a larger surface area for the dielectric between the capacitor structure 816 electrodes. As will be appreciated, other configurations of the capacitor structure 816 are possible.

As discussed herein, the thickness and/or changes in the dielectric material along the length of the sleeve 810 can be used to change the capacitance (C) so as to compensate for changes in the cross-sectional area defined by the inductor coil 802. As discussed herein, these changes in dielectric material and/or the distance between the electrodes of the capacitor structure 816 allow for changes in the capacitance value (C) of the capacitor structure 816.

Suitable materials for the conductive layer 869 include, but are not limited to, electrically conductive metals and metal alloys. Examples include, but are not limited to, platinum, tungsten, titanium, tantalum, niobium, and gold. In addition, the resonator device 800 can further include an electrically insulating layer over the conductive layer 869.

Embodiments of the resonator device discussed herein can be used in association, or in conjunction, with a vascular stent or other medical device. For example, the resonator device can be provided over at least a part of the vascular stent. In another example, the resonator device can be provided within at least a part of the vascular stent. The resonator device in conjunction with the vascular stent can then operate in the presence of an electromagnetic field produced by an MRI system to reduce the artifacting (signal loss) in images obtained by an MRI system.

Figure 9:
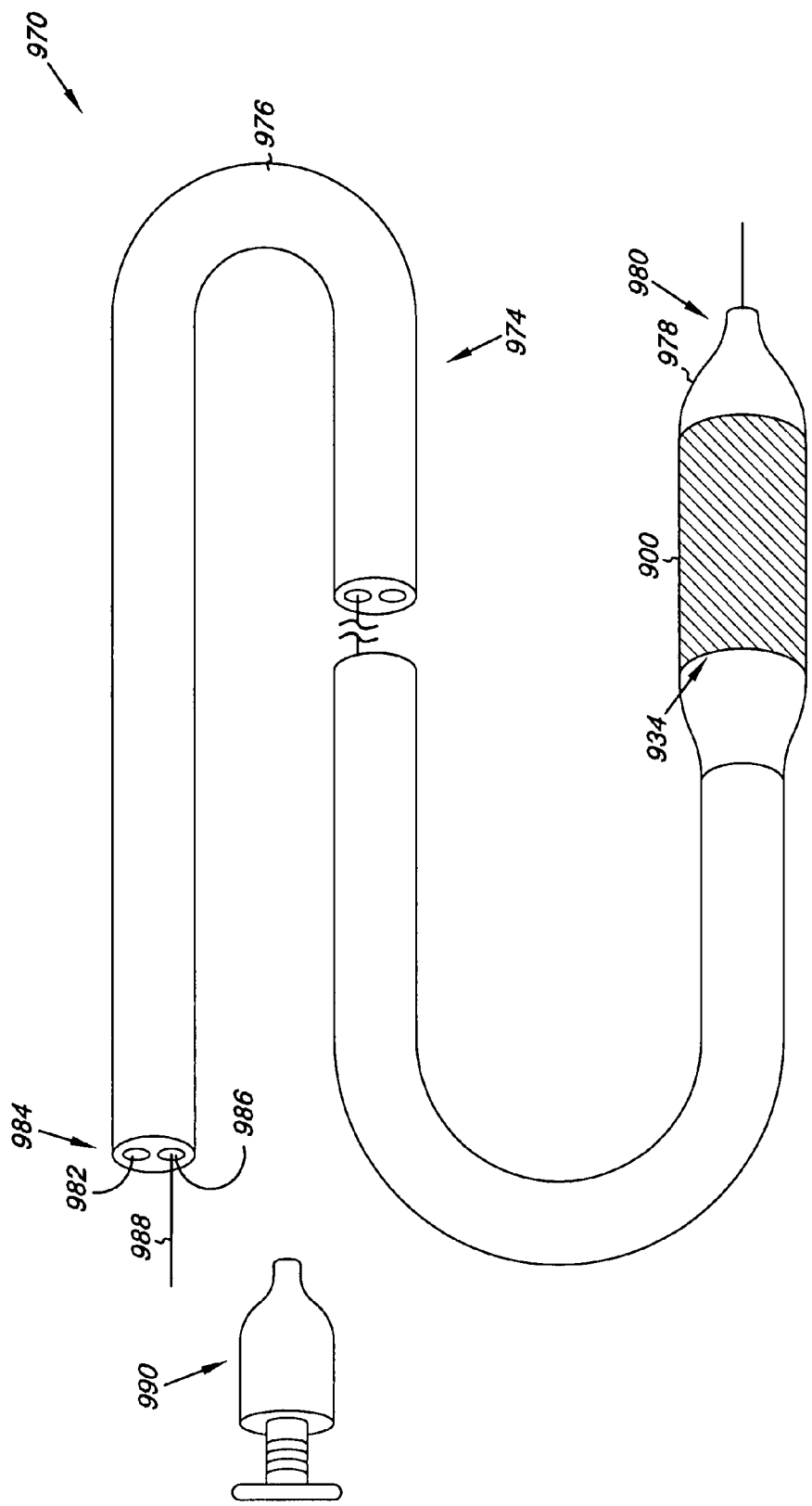
FIG. 9 illustrates an embodiment of a system including a resonator device according to the present disclosure.

FIG. 9 illustrates a system 970 having a catheter 974 with an elongate body 976, an inflatable balloon 978 positioned adjacent a distal end 980, and a lumen 982 longitudinally extending in the elongate body 976 of the catheter 974 from the inflatable balloon 978 to a proximal end 984. In the present example, the inflatable balloon 978 can be at least partially positioned within the lumen 934 of the resonator device 900.

The catheter 974 can further include a guidewire lumen 986 to receive a guidewire 988. Guidewire 988 and guidewire lumen 986 assist in positioning the resonator device 900, as discussed herein, at a predetermined location within the body. Once in position, the inflatable balloon 978 can be inflated through the use of an inflation pump 990 that can releasably couple to the lumen 982. As the inflatable balloon 978 inflates, the resonator device 900 expands to the second circumference, as discussed herein, so as to position the resonator device 900 in the patient.

As discussed herein, embodiments of the resonator device and the stent can be implanted into a body. As will be appreciated, a variety of procedures can be used to implant an embodiment of the resonator device in association with the stent. For example, certain embodiments of the resonator device can be implanted adjacent a stent that has already been implanted in a body. Alternatively, both the stent and certain embodiments of the resonator device can be implanted simultaneously. For example, both the stent and the resonator device could be loaded onto an implant catheter (e.g., a balloon catheter) for implanting in the body.

While the present disclosure has been shown and described in detail above, it will be clear to the person skilled in the art that changes and modifications may be made without departing from the scope of the disclosure. As such, that which is set forth in the foregoing description and accompanying drawings is offered by way of illustration only and not as a limitation. The actual scope of the disclosure is intended to be defined by the following claims, along with the full range of equivalents to which such claims are entitled.

In addition, one of ordinary skill in the art will appreciate upon reading and understanding this disclosure that other variations for the disclosure described herein can be included within the scope of the present disclosure. For example, the resonator device can be coated with a non-thrombogenic biocompatible material, as are known or will be known, one or more pharmaceuticals and/or biological compounds or molecules.

Embodiments and illustrations described herein can further be modified and/or added to according to co-pending U.S. patent application Ser. No. 09/779,204, entitled "Vascular Stent with Composite Structure for Magnetic Reasonance Imaging Capabilities" [sic], and U.S. patent application Ser. No. 11/207,304, entitled "Resonator for Medical Device" (e.g., the structural support structure described therein), which are both incorporated herein by reference in its entirety.

In the foregoing Detailed Description, various features are grouped together in several embodiments for the purpose of streamlining the disclosure. This method of disclosure is not to be interpreted as reflecting an intention that the embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A resonator device, comprising:
   an inductor coil;
   a conductive member that extends from the inductor coil, a portion of the conductive member configured as a spiral extending along a longitudinal axis that defines a passage through which at least a portion of the induction coil passes to form a capacitor structure; and
   a sleeve of dielectric material between one of the portion of the conductive member and the portion of the induction coil to form a capacitor structure, where the dielectric layer changes at least one of a thickness and a type along a length of the passage to compensate for changes in a cross-sectional area defined by the inductor coil by changes in a capacitance of the resonator device.

2. The resonator device of claim 1, further including a guide collar that extends from the conductive member forming the spiral, where the portion of the induction coil passes through the guide collar and into the passage.

3. The resonator device of claim 2, where the guide collar extends from a distal end of the conductive member forming the spiral.

4. The resonator device of claim 1, where the conductive member forming the spiral has a non-uniform coil density along a length of the spiral.

5. A resonator device, comprising:
   an inductor coil;
   a conductive member that extends from the inductor coil, a portion of the conductive member configured as a spiral extending along a longitudinal axis that defines a passage through which at least a portion of the induction coil passes, where the conductive member forming the spiral tapers to allow changes in a distance between the portion of the induction coil that passes into the passage and the conductive member defining the passage; and
   a dielectric layer between one of the portion of the conductive member and the portion of the induction coil to form a capacitor structure.

6. A resonator device, comprising:
   an inductor coil;
   a conductive member that extends from the inductor coil, a portion of the conductive member configured as a spiral extending along a longitudinal axis that defines a passage through which at least a portion of the induction coil passes; and
   a dielectric layer between one of the portion of the conductive member and the portion of the induction coil to form a capacitor structure, where the resonance device has a resonance frequency (F) that matches a Larmor frequency of an MRI system, where the F is given by the inverse square root of the product inductance (L) times (x) capacitance (C): $F = 1/(2 \cdot (\pi) \cdot (L \cdot C)^{0.5})$.

7. The resonator device of claim 6, where the F of the resonance device matches the Larmor frequency of the MRI system due to predetermined changes in the capacitance (C) value that correspond to and compensate for changes in the inductance (L) value as a cross-sectional area of the induction coil changes.

* * * * *